(12) United States Patent
Guenthner et al.

(10) Patent No.: US 6,183,513 B1
(45) Date of Patent: Feb. 6, 2001

(54) INTRAOCULAR LENS PACKAGING SYSTEM, METHOD OF PRODUCING, AND METHOD OF USING

(75) Inventors: Gary L. Guenthner, Largo; Glenn Thomas Stefaniak, Tarpon Springs, both of FL (US); Brian Monroe McMaster, Henrietta, NY (US); Bradly Adams, New Port Richey, FL (US)

(73) Assignee: Bausch & Lomb Surgical, Inc., Claremont, CA (US)

( * ) Notice: Under 35 U.S.C. 154(b), the term of this patent shall be extended for 0 days.

(21) Appl. No.: 09/092,514

(22) Filed: Jun. 5, 1998

(51) Int. Cl.[7] ........................................ A61F 2/16
(52) U.S. Cl. ................ 623/6.12; 606/107; 206/316.1
(58) Field of Search ................. 623/6, 4, 66, 6.11, 623/6.12, 4.1; 606/107, 211; 215/316, 329, 335, 215; 206/5.1, 316.1, 438

(56) References Cited

U.S. PATENT DOCUMENTS

| 4,257,521 | * | 3/1981 | Poler | 206/5.1 |
|---|---|---|---|---|
| 4,326,306 | * | 4/1982 | Poler | 206/5.1 X |
| 4,423,809 | * | 1/1984 | Mazzocco | 206/5.1 |
| 4,697,697 | * | 10/1987 | Graham et al. | 206/5.1 |
| 4,844,242 | * | 7/1989 | Chen et al. | 206/5.1 |
| 5,281,227 | * | 1/1994 | Sussman | 606/107 |
| 5,290,293 | | 3/1994 | Van Noy et al. | 606/107 |
| 5,454,818 | | 10/1995 | Hambleton et al. | 606/107 |
| 5,607,433 | | 3/1997 | Polla et al. | 606/107 |

* cited by examiner

Primary Examiner—Jeffrey A. Smith
(74) Attorney, Agent, or Firm—Rita D. Vacca

(57) ABSTRACT

An intraocular lens implant packaging system equipped with a mechanism for holding and folding a foldable intraocular lens implant having been packaged and sterilized therein. The packaging system includes a bottle or vial, a sealing apparatus, and a retainer member that removably locks onto the bottle and maintains the sealing apparatus in proper sealing alignment over an open end of the bottle. The intraocular lens implant stored within the bottle is protected during sterilization, storage and transportation such that the intraocular lens is not dislocated or damaged before its intended use.

30 Claims, 7 Drawing Sheets

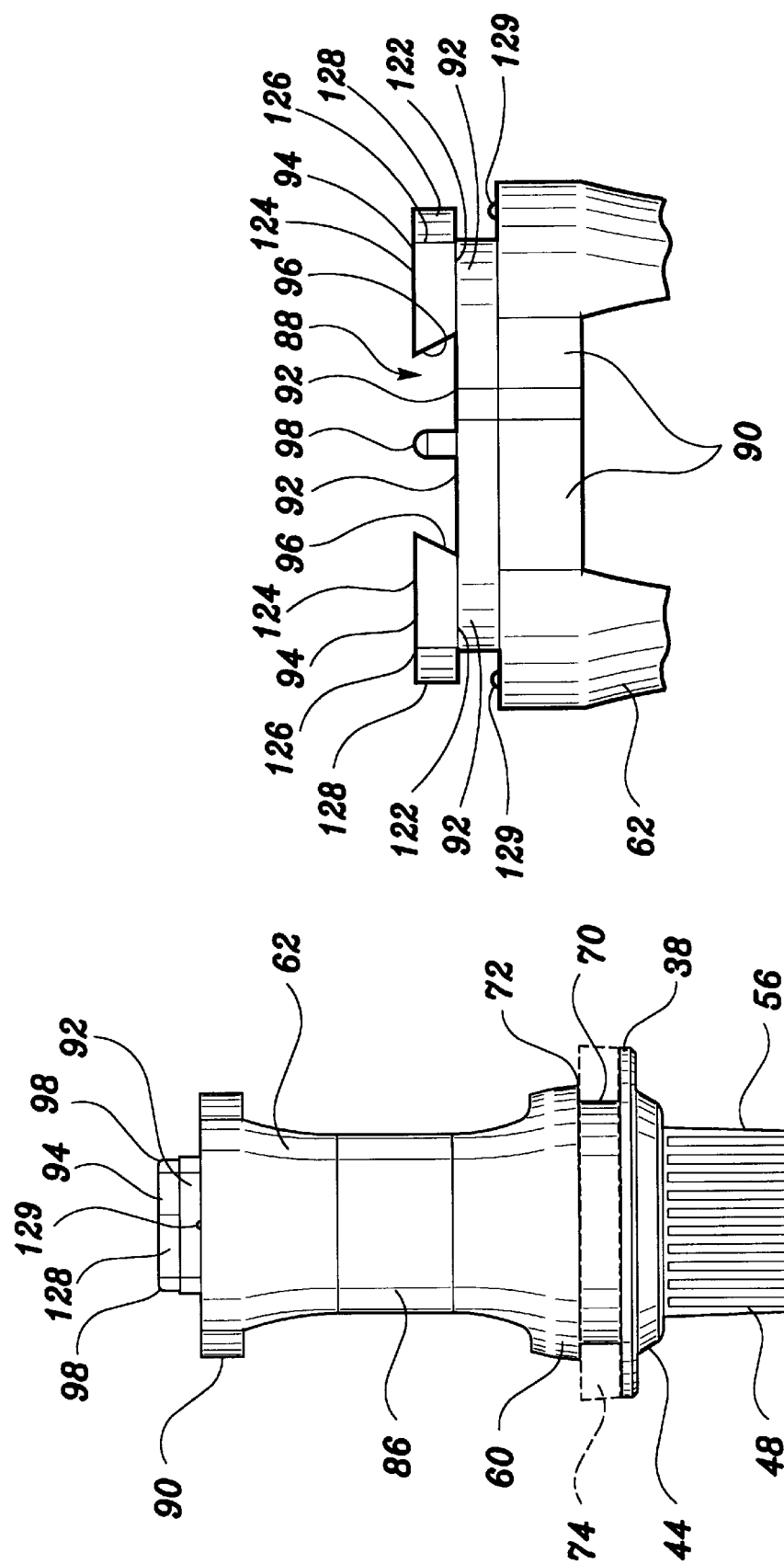

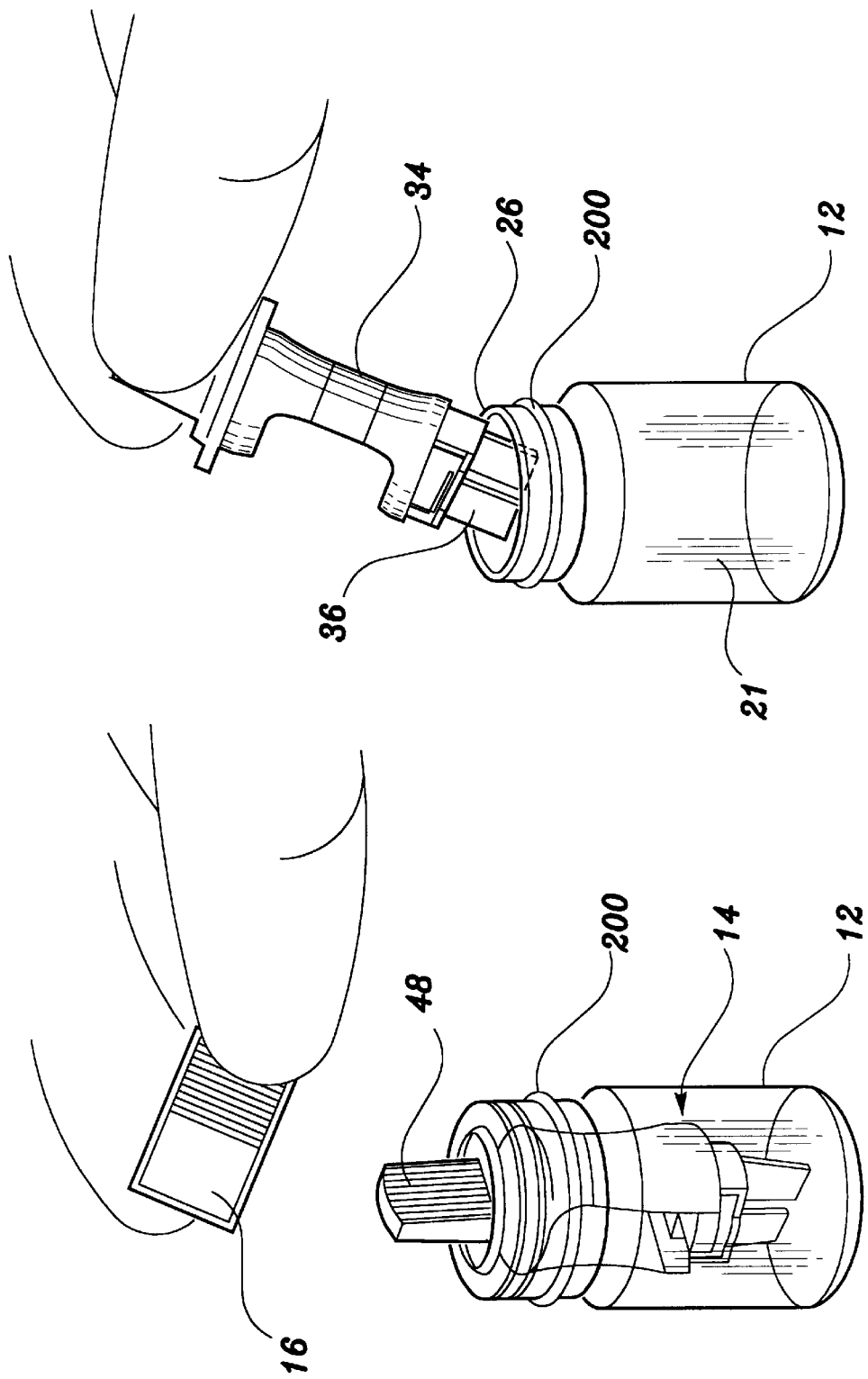

INTRAOCULAR LENS PACKAGING SYSTEM, METHOD OF PRODUCING, AND METHOD OF USING

FIELD OF THE INVENTION

The present invention relates to an intraocular lens (IOL) implant packaging system, and more particularly, to a foldable IOL storage container equipped with means for holding and folding a foldable IOL having been packaged therein.

BACKGROUND OF THE INVENTION

For many years, the usual method of treating a diseased intraocular lens has been to remove the diseased lens and replace it with an IOL implant. Two surgical procedures have each been found useful in the removal of a diseased lens, i.e., extracapsular cataract extraction and phacoemulsification. Extracapsular cataract extraction involves the removal of a diseased lens in a relatively intact condition through the use of forceps or an instrument similar thereto. Phacoemulsification involves contacting a diseased lens of an eye with a vibrating cutting tip of an ultrasonically driven surgical handpiece to emulsify the lens. Once emulsified, the lens is aspirated from the eye. Both surgical procedures require the cornea (or sclera) and the anterior lens capsule of the eye to be opened to allow access to the interior of the lens capsule. Once within the lens capsule, the diseased lens is removed and an IOL implant is positioned therein. Originally, extracapsular cataract extraction was the preferred and most commonly used surgical technique for intraocular lens removal. However, over time surgeons found that by reducing the size of the incision made in the cornea and lens capsule, or capsular bag, complications were also reduced. Postoperative complications commonly associated with large incision ocular surgery include for example induced astigmatism. Accordingly, today, phacoemulsification is the more popular and most commonly used surgical technique for intraocular lens removal due in part to the relatively small incision required to be made through the cornea and lens capsule.

Once diseased lens tissue is removed from the lens capsule of an eye, an IOL implant is typically introduced. A typical IOL implant includes an optic portion and at least one support member or haptic for positioning and supporting the IOL within the lens capsule or capsular bag. The diameter of the optic portion varies depending on the design of the IOL within the range of about 5 millimeters (mm) to 7 mm. It is a goal of the surgeon to make and utilize as small of an incision as possible, such as about 3 mm, during the removal of diseased lens material. If a 5 to 7 mm rigid IOL were to be implanted in a lens capsule, the surgeon would have to widen a 3 mm incision significantly to allow the IOL to be inserted. However, such an enlargement of the incision would reduce one of the advantages of phacoemulsification surgical technique. Therefore, foldable IOLs have been developed which may be folded, inserted into an eye's capsular bag and then released or unfolded with minimal or no widening of the original approximately 3 mm incision.

As known to those skilled in the art, foldable IOLs generally are made from polyurethane elastomers, silicone elastomers, hydrogel polymers, collagen compounds, organic gel compounds, synthetic gel compounds or a combination thereof. The resultant IOL preferably has a soft foldable lens optic portion. However, lenses that are soft and foldable can in some cases be difficult to fold using known folding and insertion devices due to surface tackiness. However, most foldable lenses described above may be rolled, compressed or folded by a special syringe or forceps, and then placed into an eye's capsular bag by releasing the same without enlarging the original incision. IOL folding devices are described in detail in U.S. Pat. Nos. 5,281,227, 5,290,293, and 5,607,433. While such folding and insertion devices work well for many of the IOLs manufactured from the materials discussed above, the same is not true for all foldable IOLS depending on the particular composition and /or design of the IOL. Furthermore, many such folding and insertion devices are bulky and require much practice to perfect the use thereof.

In order for a surgeon to fold an IOL without the aid of a special folding device such as those described above, forceps or a similar type tool is used to remove the IOL from the IOL packaging. A second tool or forceps is then used to fold the IOL. The folded IOL is then typically transferred for proper gripping to a third tool or set of forceps for insertion into the capsular bag of an eye. Such a technique, while safe and effective, requires a great deal of practice to perfect.

Accordingly, a long felt need exists for an inexpensive tool or method that allows a surgeon to easily remove an IOL from its packaging, fold the IOL and implant the same within an eye without numerous transfers between tools.

BRIEF SUMMARY OF THE INVENTION

The present invention is a packaging system for IOL implants. The preferred embodiment of the subject packaging system includes a bottle or vial, a sealing apparatus and a cap member which removably locks onto the bottle and maintains the sealing apparatus in proper sealing alignment over an open end of the bottle. The sealing apparatus is generally a disk with one planar surface thereof having two arms extending therefrom. The arms are designed to provide a pair of jaw members for holding an IOL. A removable retainer member extends around a portion of the jaw members to retain the IOL in proper orientation between the jaw members by maintaining the relative position of the jaw members. The retainer member protects the IOL within the bottle during sterilization, storage and transportation such that the IOL is not dislocated or damaged before its intended use.

In using the subject packaging system, the cap member is removed from the bottle. The sealing apparatus is then removed from the bottle and inverted so that the arms extend upwardly. The retainer member is removed from around and between the jaw members such as by twisting in a counter-clockwise direction and then lifting the same. Once the retainer member is removed, the arms may then be squeezed together so that the jaw members move in closer proximity to one another. In bringing the jaws in closer proximity, the IOL is supported therebetween in a folded position. A pair of insertion forceps or the like is then used by a surgeon to remove the folded IOL from its packaging for insertion within a patient's eye.

Accordingly, it is an object of the present invention to provide packaging for an IOL, which protects the same from damage.

Another object of the present invention is to provide a single storage, holding and folding device for a foldable IOL.

Another object of the present invention is to provide an IOL folding device, which is easy to use.

Another object of the present invention is to provide IOL packaging that keeps a foldable IOL wet, free of contamination, and protected from damage during sterilization, storage and handling.

Another object of the present invention is to provide IOL packaging that delivers an accurately and precisely folded wet IOL to a surgeon and to eliminate the need for a separate folding tool.

Still another object of the present invention is to provide IOL packaging that requires the use of only one hand to fold the lens so that the surgeon's other hand can hold insertion forceps for removal of an IOL therefrom for insertion into a patient's eye.

These and other objectives and advantages of the present invention, some of which are specifically described and others that are not, will become apparent from the detailed description, drawings and claims that follow wherein like features are designated by like numerals.

BRIEF DESCRIPTION OF THE DRAWINGS

FIG. 3 is a side plan view of the sealing apparatus of the IOL packaging system of FIG. 2 rotated along its axis 90 degrees;

FIG. 4 is an enlarged side plan view of the sealing apparatus of FIG. 2 taken along line 4—4;

FIG. 9 is a perspective view of the IOL packaging system of FIG. 1 illustrating separation of the cap member;

FIG. 10 is a perspective view of the IOL packaging system of FIG. 9 illustrating withdrawal of the sealing apparatus;

DETAILED DESCRIPTION

Figure 2:
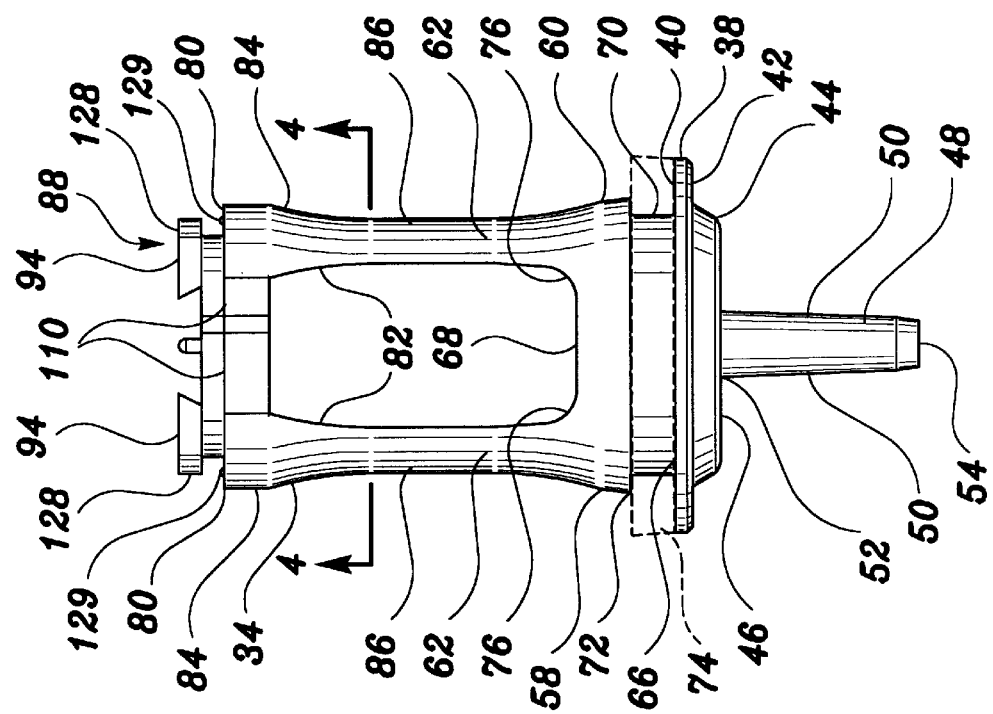
FIG. 2 is a side plan view of the sealing apparatus of the IOL packaging system of FIG. 1 in an inverted position with the retainer member removed.
Figure 1:
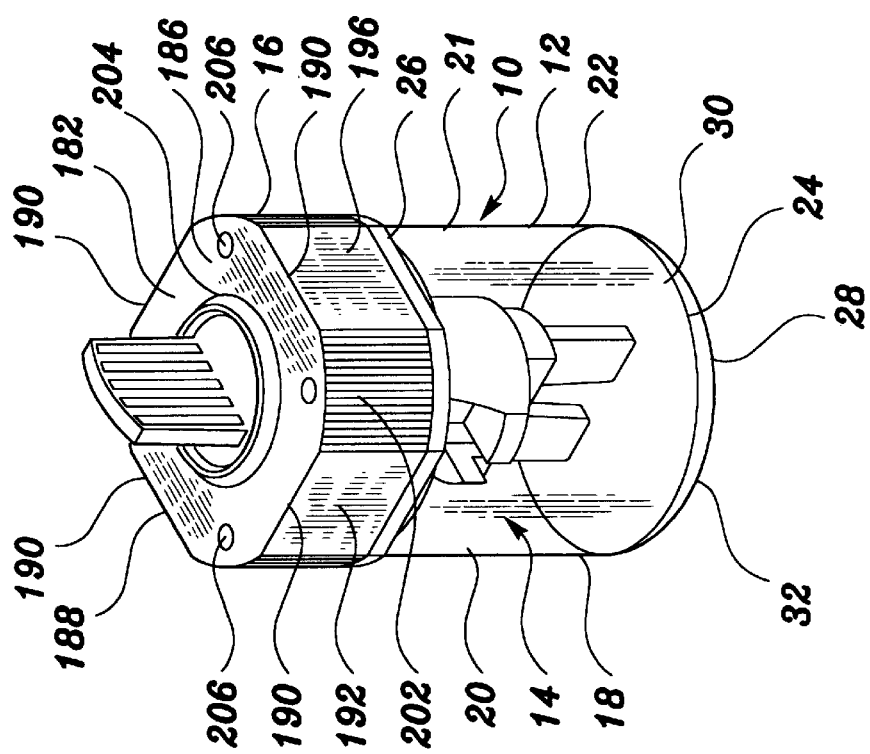
FIG. 1 is a perspective view of a preferred embodiment of the IOL packaging system of the present invention.

As best illustrated in FIG. 1, the preferred embodiment of the IOL packaging system of the present invention is generally designated at 10. Packaging system 10 consists of a bottle or vial portion 12, sealing apparatus 14 and cap member 16. Bottle portion 12 consists of a generally tubular body portion 18 having an interior surface 20, exterior surface 22 and opposed ends 24 and 26. Opposed end 24 is closed by a generally disc-shaped base member 28 having interior surface 30 and exterior surface 32. Opposed end 26 is open. Interior surfaces 20 and 30 define interior bottle volume 21.

Although bottle portion 12 is illustrated as generally tubular, any other geometric shape which allows for easy placement of the same in a larger container such as a box with a plurality of other bottle portions 12 for shipping and/or storage would likewise be suitable. Examples of other suitable geometric shapes include but are not limited to square, rectangle or triangle, each of which would help prevent the bottle if tipped from rolling around on a table or tray within a sterile field of a surgical room. Additionally, bottle portion 12 in the preferred embodiment is made of clear transparent glass which is preferred to allow for visual inspection of the contents without having to open bottle portion 12. It is also possible however, that bottle portion 12 be opaque and/or made of other suitable materials such as but not limited to various plastic or resin materials.

Figure 6:
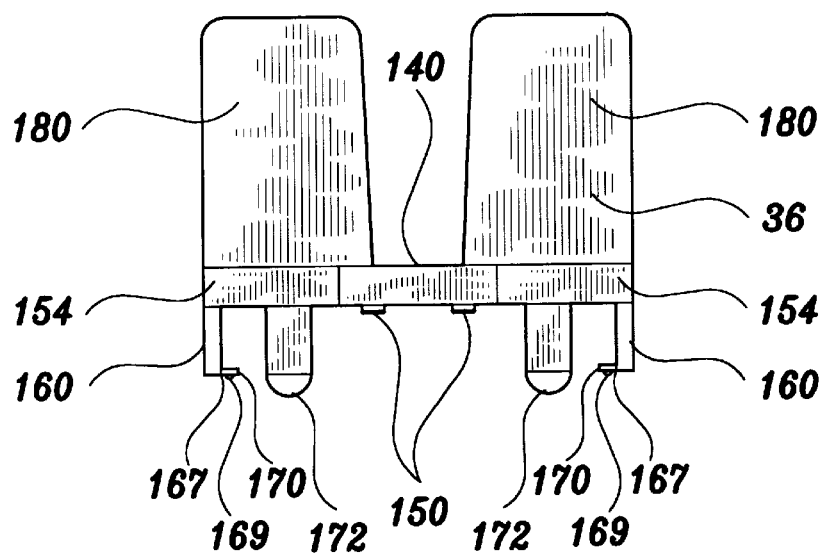
FIG. 6 is an enlarged side plan view of the retainer member removed from the sealing apparatus of FIG. 1 in an inverted position.
Figure 7:
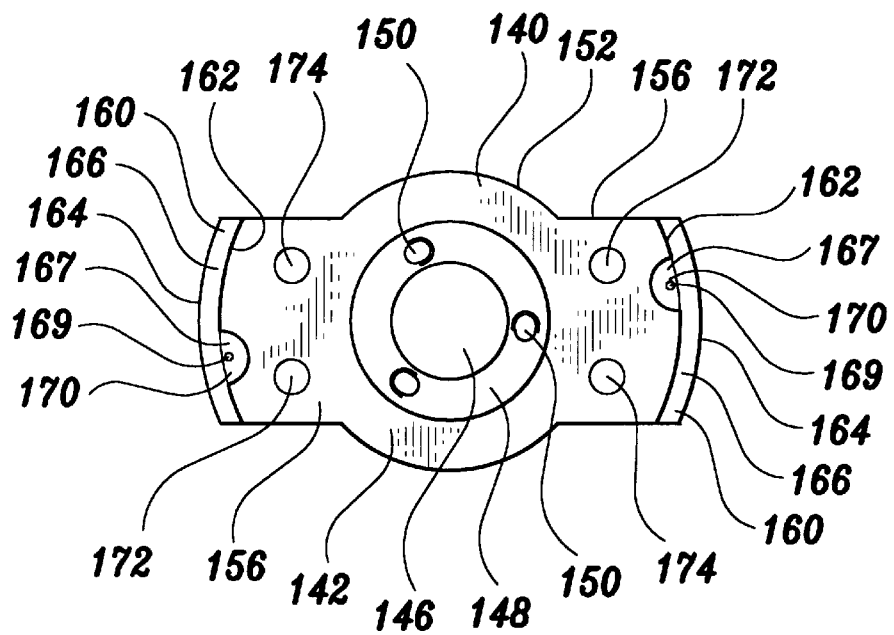
FIG. 7 is an enlarged bottom plan view of the retainer member of FIG. 6.
Figure 8:
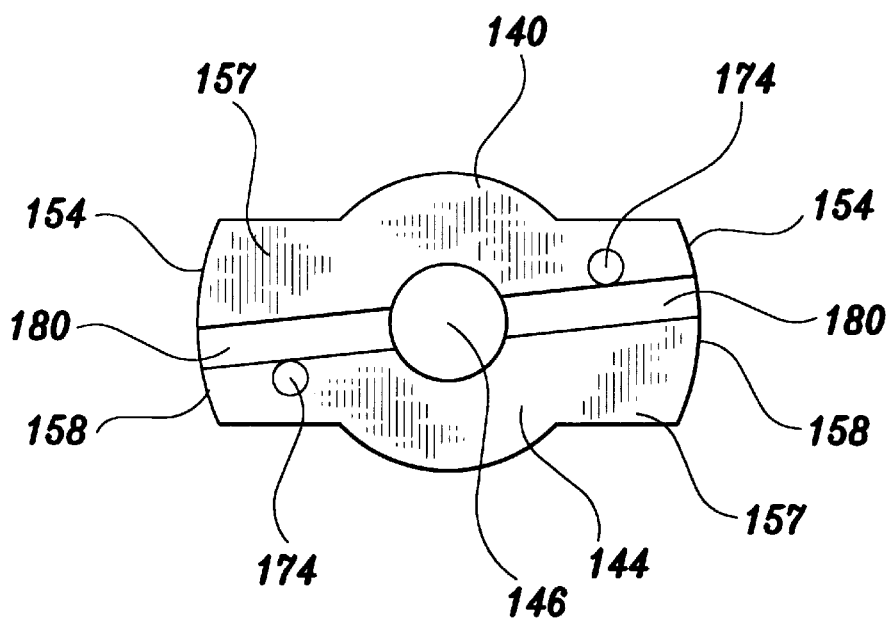
FIG. 8 is an enlarged top plan view of the retainer member of FIG. 6.

Bottle portion 12 works in conjunction with sealing apparatus 14. Sealing apparatus 14 consists generally of a holder portion 34 as best illustrated in FIGS. 2 through 5, and a retainer member 36 as best illustrated in FIGS. 6 through 8. Holder portion 34 and retainer member 36 are preferably constructed of plastic although other sterilizable materials could be used such as but not limited to stainless steel. Holder portion 34 and retainer member 36 may each be constructed of various components as described in detail below or be of a more preferred molded unitary construction. Holder portion 34 generally comprises a disk portion 38 having interior surface 40 and exterior surface 42. Extending from exterior surface 42 of disk portion 38 is handle base 44, which has exterior surface 46. Extending from exterior surface 46 is handle 48. Handle 48 may have any number of suitable configurations, which allows gripping thereof and removal of holder portion 34 from bottle volume 21. Handle 48 in the preferred embodiment is generally a planar tab having opposed planar surfaces 50, attached edge 52 attached to exterior surface 46 and opposed free edge 54. Planar surfaces 50 are preferably textured in some manner such as with gripping grooves 56 to facilitate gripping of handle 48.

Extending from interior surface 40 of disk portion 38 is base support 60. Base support 60 is again generally disk shaped and has attached surface 66 and free surface 68. Around the periphery 58 of base support 60 at attached surface 66 is a groove 70 for accepting the interior edge 72 of gasket 74 shown in FIGS. 2 and 3 in phantom lines. Extending from free surface 68 of base support 60 are opposed arm members 62. Opposed arm members 62 have attached edges 76, free edges 80, opposed planar interior surfaces 82 and rounded exterior surfaces 84. Exterior surfaces 84 are rounded to follow the periphery 58 of base support 60. Exterior surfaces 84 of opposed arm members 62 are also preferably concavely contoured with respect to free edges 80 and attached edges 76 at mid regions 86 for easy grasping.

Free edges 80 of opposed arm members 62, have in general jaw members 88. Jaw members 88 comprise flange members 90, optic supports 92, free ends 94, lens notches 96, alignment pins 98 and positioning grooves 100.

Flange members 90 each have opposed attached edges 102 and free edges 104. Attached edges 102 are attached to interior surfaces 82 of opposed arm members 62 at right edges 106 so flange members 90 are perpendicular to arm members 62 and form a plane with free edges 80. Flange members 90 are approximately 50 to 75 but more preferably approximately 66 percent as wide as the width of interior surfaces 82. Exterior edges 108 of flange members 90 have the same degree of curvature as rounded exterior surfaces 84 so as to form a continuous arc therewith. Extending from planar surfaces 110 of flange members 90, are optic supports 92.

Optic supports 92 are generally tabs approximately 30 to 60 but more preferably approximately 50 percent as wide as the width of planar surfaces 110 and are positioned along free edges 104 and left free edges 112 of flange members 90. Opposed arcs 114 are formed in free edges 116 of optic supports 92 and free edges 104 of flange members 90. Opposed arcs 114 form an opening 101 through which the diopter power of IOL 130 may be measured without having to remove IOL 130 from the apparatus. Raised alignment pins 98 extend perpendicularly from planar surfaces 118 near right free edges 120 of optic supports 92. Also extending from planar surfaces 118 are free ends 94. Free ends 94 are formed to have lens notches 96 at the attached bases 122 thereof. Free ends 94 have planar surfaces 124 opposite attached bases 122 and have positioning grooves 100 formed therein. Extending outwardly from exterior edges 126 of free ends 94 and in the same plane as planar surfaces 124 are locking tabs 128. Opposite interior planar surface 127 of locking tabs 128 on free edges 80 is ridge 129.

Figure 5:
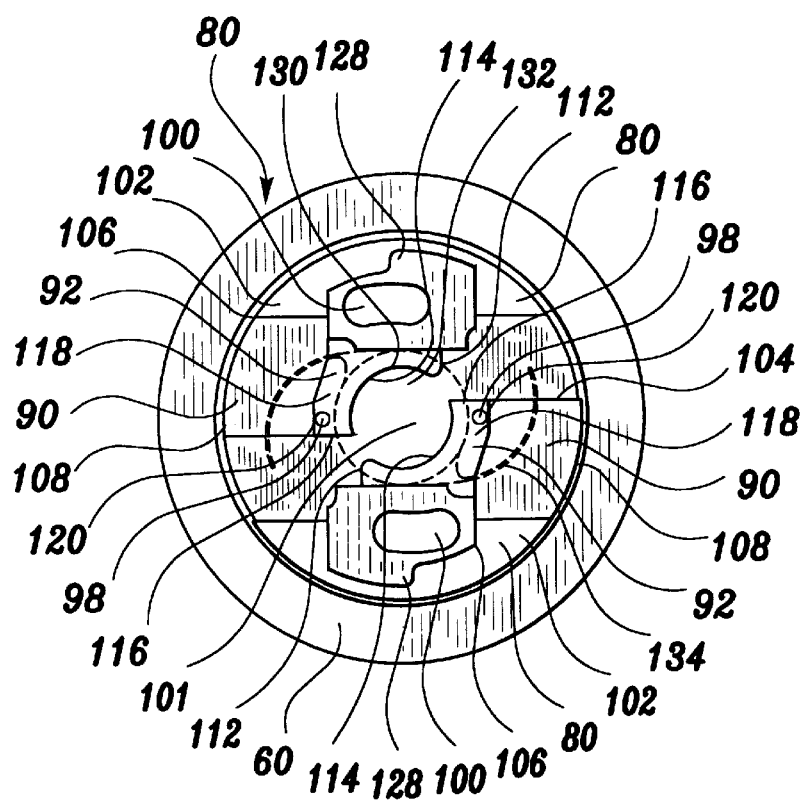
FIG. 5 is an enlarged top plan view of the sealing apparatus of FIG. 3 with an IOL shown in phantom lines.

Referring to FIG. 5, a top view of holder portion 34 illustrates in general jaw members 88 with IOL 130 shown in phantom lines positioned therebetween. IOL 130 as illustrated, consists generally of an optic portion 132 and at least one haptic 134. A foldable IOL such as IOL 130 may be folded along an axis of optic 132 equal distance between and perpendicular to haptics 134. By folding IOL 130 in such a manner, the width of IOL 130 is generally decreased by approximately fifty percent. This width reduction of IOL 130 allows the same to be implanted through a smaller incision through the cornea and anterior lens capsule of an eye.

Best illustrated in FIGS. 6 through 8, is retainer member 36 of sealing apparatus 14. The preferred embodiment of retainer member 36 consists of a disk portion 140 having opposed interior and exterior planar surfaces 142 and 144 respectively. An aperture 146 is formed through the center of disk portion 140. Groove 148 is formed around aperture 146 on interior planar surface 142. Within groove 148 are at least two but most preferably three pin members 150. Extending outwardly from the outer edge 152 of disk portion 140 in the same plane as interior and exterior planar surfaces 142 and 144 are opposed tab members 154. Tab members 154 have opposed interior and exterior planar surfaces 156 and 157 respectively. Extending perpendicularly from interior planar surfaces 156 along free edges 158 of tab members 154 are locking arms 160. Locking arms 160 and free edges 158 are rounded to follow the contour of rounded exterior surfaces 84 of arm members 62. Locking arms 160 have opposed interior and exterior surfaces 162 and 164 respectively and free edges 166. Extending perpendicularly from interior surfaces 162 at free edges 166 are lock tabs 170. Extending perpendicularly from exterior surface 167 of lock tabs 170 are positioning tips 169. Extending perpendicularly from interior surfaces 156 between free edges 158 and groove 148 are locking pins 172. Also between free edges 158 and groove 148, at least one but preferably two apertures 174 are formed through tab members 154. Apertures 174 provide a means for fluid flow in the area surrounding optic portion 132 to prevent possible damage to IOL 130. Extending perpendicularly from exterior surfaces 144 and 157 are grip wings 180.

As best illustrated in FIG. 1, bottle 12 and sealing apparatus 14 are removably locked into position with cap member 16. Cap member 16 comprises a disk member 182 having interior planar surface 184 (not shown), exterior planar surface 186 and free edge 188. Free edge 188 is reduced at four opposed points to form four flattened edges 190 thereon. Extending perpendicularly from interior planar surface 184 along free edges 188 and flattened edges 190 is skirt member 192. Skirt member 192 has interior surface 194 (not shown) which is of a generally circular cross-section and exterior surface 196 which is of a generally eight-sided cross-section. Interior surface 194 is threaded 198 (not shown) for removable engagement with threaded means 200 located on exterior surface 22 near open end 26 of bottle portion 12. Although in the preferred embodiment of the subject IOL packaging system 10 threaded means are depicted for purposes of engaging cap member 16 and bottle portion 12, any means of engagement capable of maintaining sterility known to those skilled in the art would be suitable. Gripping grooves 202 may be applied to all or a portion of exterior surface 196 for easy manipulation of cap member 16 during use. Aperture 204 is formed in the center of disk member 182. Likewise, at least one but most preferably four holes 206 are formed in disk member 182 preferably between free edges 188 and aperture 204. Holes 206 provide means for steam penetration into cap member 16 during sterilization of the fully assembled packaging system 10. Any alternative placement of holes 206 in cap member 16 that would serve this purpose would likewise be suitable.

The preferred embodiment of the IOL packaging system of the present invention is assembled or manufactured by first placing IOL 130 in jaw members 88 as best illustrated in FIG. 5. IOL 130 is properly positioned in jaw members 88 when optic 132 is supported on optic supports 92 and positioned within lens notches 96 so as to allow haptics 134 to extend freely over flange members 90. Exterior edges 108 of flange members 90 are several millimeters to the exterior of haptics 134 to protect haptics 134 from possible damage during sterilization, shipping, storage and end use, such as but not limited to during the removal of sealing apparatus 14 from bottle 12. Alignment pins 98 prevent IOL 130 from any substantial movement such as sliding out of lens notches 96. Retainer member 36 is then locked onto holder portion 34 by placing locking pins 172 within positioning grooves 100 and rotating the same using grip wings 180 to position lock tabs 170 between free edges 80 and locking tabs 128. Lock tabs 170 are maintained between free edges 80 and locking tabs 128 by positioning tips 169. Positioning tips 169 can not slip over ridge 129 to release lock tabs 170 without manual force being applied. Pin members 150 prevent any substantial movement of IOL 130 between holder portion 34 and retainer member 36. Retainer member 36 serves to protect IOL 130 and to maintain jaw members 88 in proper position and alignment during sterilization, shipping and storage.

After retainer member 36 is locked onto holder portion 34 forming sealing apparatus 14, the same is placed within bottle volume 21, which may contain deionized water, saline solution or other desired fluid. Sealing apparatus 14 is positioned within bottle 12 so as to allow gasket 74 to rest on end 26 of bottle portion 12. Cap member 16 is then placed over sealing apparatus 14 whereby exterior surface 46 of handle base 44 and handle 48 extend outwardly through aperture 204. Skirt member 192 of retainer member 16 removably engages bottle portion 12 with threaded means 198 and 200 to form an air tight seal 201 (not shown) between sealing apparatus 14 and bottle portion 12. IOL 130 packaged in the subject packaging system 10 as describe above may be sterilized, by any suitable method known to those skilled in the art such as by autoclaving, shipped and stored until use. It is contemplated that cap member 16 may be constructed and used without aperture 204 in a case where sealing apparatus 14 has no handle 48. In such a case, sealing apparatus would be manipulated using disk portion 38. It is further contemplated that in such a case, cap member 16 and sealing apparatus 14 could be constructed as a unitary device whereby the same would be manipulated using cap portion 16.

Figure 12:
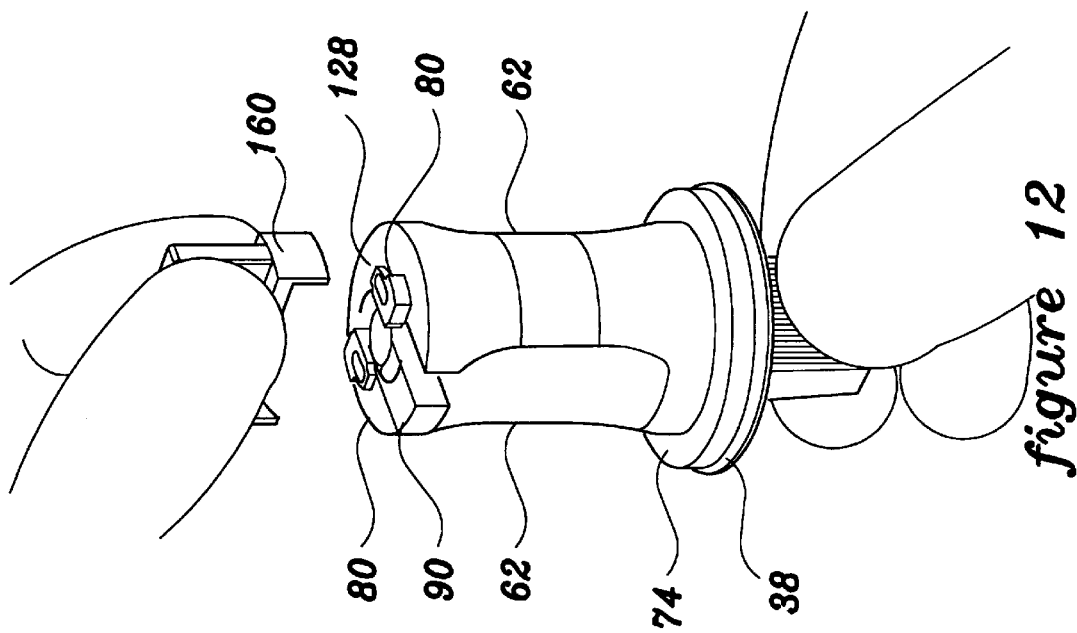
FIG. 12 is a perspective view of the sealing apparatus of FIG. 11 illustrating separation of the retainer member.
Figure 11:
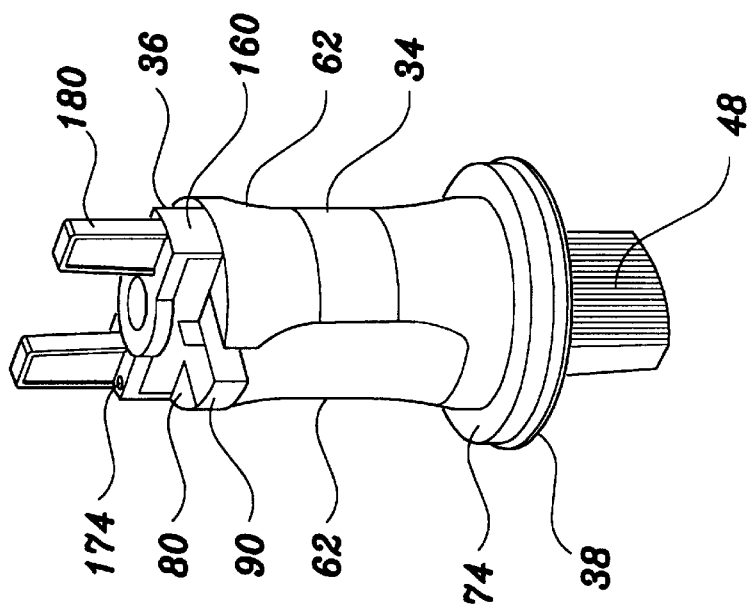
FIG. 11 is an enlarged perspective view of the sealing apparatus of FIG. 1 in an inverted position.

In using the subject IOL packaging system 10 as best illustrated in FIGS. 9 through 14 and beginning with FIG. 9, cap member 16 is first removed from bottle portion 12. Cap member 16 is removed from bottle portion 12 by rotating cap member 16 counter-clockwise relative to bottle portion 12 to disengage threaded means 198 and 200. Upon disengaging threaded means 198 and 200, seal 201 maintaining the sterility of bottle volume 21 and its contents is broken. As illustrated in FIG. 10, after the removal of cap member 16, sealing apparatus 14 may be removed from bottle volume 21. Sealing apparatus 14 is removed from bottle volume 21 by grasping handle 48 and lifting the same out of bottle volume 21. As illustrated in FIGS. 11 and 12, the sealing apparatus 14 is inverted such that handle 48 is positioned below retainer member 36. Retainer member 36 is then removed from holder portion 34 by grasping grip wings 180 and rotating the same approximately twenty-five degrees counter-clockwise with respect to holder portion 34. In rotating retainer member 36, lock tabs 170 are released from their locked position between free edges 80 and locking tabs 128. Once lock tabs 170 are released from their locked position, retainer member 36 may be lifted off holder portion 34. Locking pins 172 which extend into positioning grooves 100 prevent retainer member 36 from being over-rotated or rotated clockwise when removing the same from holder portion 34.

Figure 14:
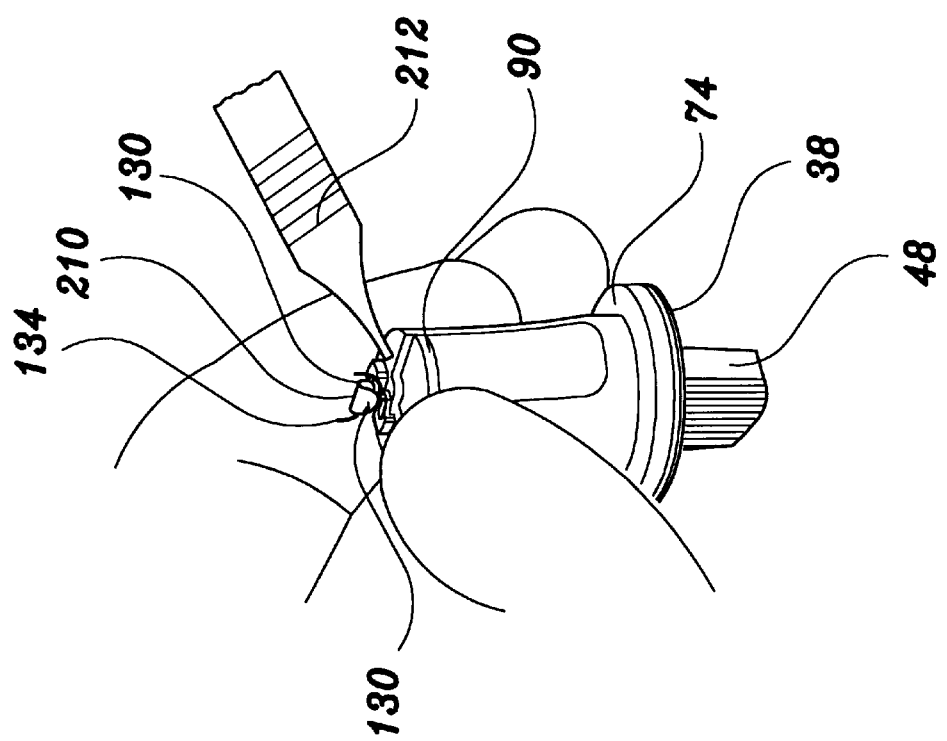
FIG. 14 is a perspective view of the compressed holder portion of FIG. 13 illustrating removal of a folded IOL therefrom.
Figure 13:
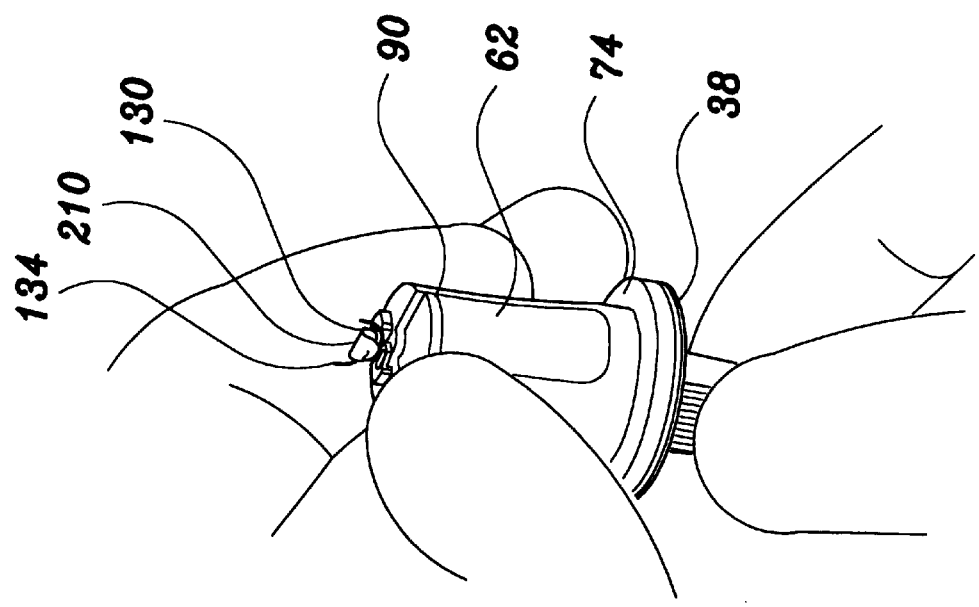
FIG. 13 is a perspective view of the holder portion of the sealing apparatus of FIG. 12 illustrating compression thereof.

Referring now to FIG. 13, the folding operation of holder portion 34 is illustrated. Arm members 62 are grasped by the user in the area of contour of mid regions 86 using the fingers of one hand. Arm members 62 are gently squeezed or biased toward one another in a non-planar, e.g., radial motion. IOL 130 positioned with optic 132 between lens notches 96 is squeezed between lens notches 96 which causes IOL 130 to be folded along a predetermined fold axis 210. As illustrated in FIG. 14, IOL 130 folded along fold axis 210 may now be removed from between lens notches 96 with a pair of forceps 212 or tool similar thereto.

As described above, the IOL packaging system of the present invention provides an easy and reliable means for storing, holding and folding a foldable IOL implant. The present description is provided for purposes of illustration and explanation. It will be apparent to those skilled in the art that modifications and changes may be made to the preferred embodiment described herein without departing from its scope and spirit.

We claim:

1. An intraocular lens implant packaging system comprising:

a bottle of a defined volume;

a cap capable of removably sealing an opening in said bottle;

two spaced arm members forming a non-surgical lens holder portion sized to fit within the defined volume of said bottle; and spaced lens notches on said spaced arm members;

whereby an intraocular lens implant may be positioned between said lens notches until use, and whereby said spaced arm members may be positioned in relatively closer proximity to one another to optionally fold said intraocular lens implant prior to use.

2. An intraocular lens implant packaging system comprising:

a bottle of a defined volume;

a cap capable of removably sealing an opening in said bottle;

two spaced arm members forming a non-surgical lens holder portion sized to fit within the defined volume of said bottle;

spaced lens notches on said spaced arm members; and an intraocular lens implant positioned between said lens notches of said spaced arm members, whereby said spaced arm members may be positioned in relatively closer proximity to one another to optionally fold said intraocular lens implant prior to use.

3. The intraocular lens implant packaging system of claim 1 or 2 wherein said bottle contains a storage fluid.

4. The intraocular lens implant packaging system of claim 1 or 2 wherein said bottle contains deionized water.

5. The intraocular lens implant packaging system of claim 1 or 2 wherein said cap includes an aperture through which a portion of said holder portion extends.

6. The intraocular lens implant packaging system of claim 1 or 2 wherein said cap and said holder portion are permanently affixed allowing simultaneous removal of said cap and said holder from said bottle.

7. The intraocular lens implant packaging system of claim 1 wherein said spaced lens notches may be biased toward one another to fold an intraocular lens implant placed therebetween.

8. The intraocular lens implant packaging system of claim 1 or 2 wherein a retainer member is positioned on said holder portion to maintain a predetermined space between said spaced lens notches.

9. The intraocular lens implant packaging system of claim 1 or 2 wherein a retainer member is positioned on said holder portion to protect an intraocular lens implant positioned within said spaced lens notches from movement and damage.

10. The intraocular lens implant packaging system of claim 1 or 2 wherein said holder portion and a retainer member engaged with said holder portion each have an aperture formed therein to allow visualization of an intraocular lens implant positioned between said spaced lens notches and to allow measurement of the lens' dioptric power.

11. The intraocular lens implant packaging system of claim 2 wherein said spaced lens notches may be biased toward one another to fold said intraocular lens implant.

12. A method of producing an intraocular lens implant packaging system comprising:

obtaining a bottle of defined volume;

placing an intraocular lens implant positioned between at least two spaced lens notches on two spaced arm members forming a non-surgical lens holder portion within said bottle; and sealing said bottle with a removable cap;

whereby said spaced arm members are suitable for positioning in a relatively closer proximity to one another to enable the same to be useful in folding said intraocular lens implant prior to use.

13. A method of producing an intraocular lens implant packaging system comprising:

obtaining a bottle of defined volume;

placing a retainer portion and an engaged intraocular lens non-surgical lens holder portion with an intraocular lens implant positioned between at least two spaced lens notches on two spaced arm members forming said non-surgical lens holder portion in said bottle; and sealing said bottle with a removable cap;

whereby said spaced arm members are suitable for positioning in a relatively closer proximity to one another to enable the same to be useful in folding said intraocular lens implant prior to use.

14. The method of claim 12 or 13 wherein said bottle contains a storage fluid.

15. The method of claim 12 or 13 wherein said bottle contains deionized water.

16. The method of claim 12 or 13 wherein said removable cap includes an aperture through which a portion of said holder portion extends.

17. The method of claim 12 or 13 wherein said removable cap and said holder portion are permanently affixed allowing simultaneous removal of said removable cap and said holder portion from said bottle.

18. The method of claim 12 or 13 wherein said spaced lens notches may be biased toward one another to fold said intraocular lens implant.

19. The method of claim 12 or 13 wherein after sealing said bottle, the same is sterilized.

20. The method of claim 12 or 13 wherein after sealing said bottle, the same is sterilized using a steam autoclave.

21. A method of using the intraocular lens packaging system of claim 2 comprising:

removing said cap from said bottle;

removing said holder portion from said bottle;

biasing said spaced lens notches toward one another to form a folded lens; and removing said folded lens from said spaced lens notches.

22. The method of claim 21 wherein said bottle contains a storage fluid.

23. The method of claim 21 wherein said bottle contains deionized water.

24. The method of claim 21 wherein said cap includes an aperture through which a portion of said holder portion extends.

25. The method of claim 21 wherein prior to biasing said spaced lens notches, a retainer member engaged to said holder portion over said spaced lens notches and said intraocular lens implant is removed.

26. A method of using the intraocular lens packaging system of claim 2 comprising:

removing said cap and said holder portion permanently affixed to said cap simultaneously from said bottle;

biasing said spaced lens notches on said holder portion toward one another to form a folded lens; and removing said folded lens from said spaced lens notches.

27. The method of claim 26 wherein said bottle contains a storage fluid.

28. The method of claim 26 wherein said bottle contains deionized water.

29. The method of claim 26 wherein said cap includes an aperture through which a portion of said holder portion extends.

30. The method of claim 26 wherein prior to biasing said spaced lens notches, a retainer member engaged to said holder portion over said spaced lens notches and said intraocular lens implant is removed.

* * * * *